United States Patent
Akemi et al.

[11] Patent Number: 5,242,951
[45] Date of Patent: Sep. 7, 1993

[54] ESTROGEN-CONTAINING GEL PREPARATION

[75] Inventors: Hitoshi Akemi; Takashi Kinoshita; Saburo Otsuka; Yoshifumi Hosaka, all of Osaka; Kunio Tsukamoto, Tokyo; Yoshihisa Nakano, Osaka, all of Japan

[73] Assignees: Nitto Denko Corporation, Osaka; Teikoku Hormone Mfg., Co., Ltd., Tokyo, both of Japan

[21] Appl. No.: 635,070

[22] Filed: Dec. 28, 1990

[30] Foreign Application Priority Data

Dec. 28, 1989 [JP] Japan ................... 1-344639
Sep. 6, 1990 [JP] Japan ................... 2-237383

[51] Int. Cl.$^5$ ............... A61K 47/32; A61L 15/03
[52] U.S. Cl. ................ 514/772.5; 424/443; 424/449
[58] Field of Search ......... 424/81, 78.32, 772.5, 424/443, 449; 514/772.5

[56] References Cited

U.S. PATENT DOCUMENTS

| | | | |
|---|---|---|---|
| 3,267,083 | 8/1966 | Imhof | 525/330.2 |
| 4,078,060 | 3/1978 | Benson et al. | 514/177 |
| 4,300,820 | 11/1981 | Shah | 424/80 |
| 4,789,667 | 12/1988 | Makino et al. | 514/420 |
| 4,917,886 | 4/1990 | Asche et al. | 424/81 |
| 5,002,986 | 3/1991 | Fujiura et al. | 525/330.2 |

FOREIGN PATENT DOCUMENTS

| | | |
|---|---|---|
| WO8600814 | 2/1986 | European Pat. Off. |
| 0223524 | 5/1987 | European Pat. Off. |
| 8905663 | 6/1989 | European Pat. Off. |
| 0328806 | 8/1989 | European Pat. Off. |
| 8907951 | 9/1989 | European Pat. Off. |
| 0364211 | 4/1990 | European Pat. Off. |
| 0379045 | 7/1990 | European Pat. Off. |
| 51-107389 | 9/1976 | Japan ........... 525/330.2 |
| 57-2303 | 1/1982 | Japan ........... 525/330.2 |
| 60-190723 | 9/1985 | Japan ........... 424/80 |

Primary Examiner—Thurman K. Page
Assistant Examiner—Peter F. Kulkosky
Attorney, Agent, or Firm—Sughrue, Mion, Zinn, Macpeak & Seas

[57] ABSTRACT

An estrogen-containing gel preparation is disclosed, which comprises a substrate having on one surface thereof a crosslinked gel layer formed by crosslinking a composition comprising the following ingredients (a) to (c), the weight ratio of the ingredient (b) to the ingredient (c) being from 1.0/0.25 to 1.0/2.0:

(a) estrogen;
(b) an acrylate polymer; and
(c) a liquid ingredient compatible with the ingredient (b).

11 Claims, 2 Drawing Sheets

5,242,951

ESTROGEN-CONTAINING GEL PREPARATION

FIELD OF THE INVENTION

The present invention relates to an estrogen-containing gel preparation which is to be applied to the surface of the skin so as to continuously administer estrogen to the living body via the skin surface.

BACKGROUND OF THE INVENTION

Recently various percutaneous preparations in the form of a preparation to be applied to the skin (for example, plaster, tape, etc.), whereby a drug is administered to the living body via the skin surface, have been developed.

As an example of an estrogen preparation in the form of the percutaneous preparation, a patch-type estradiol preparation which comprises ethanol as an aid for percutaneous absorption has been already developed and brought substantial results, as described, e.g., in JP-A-57-154122. The term "JP-A" as used herein means an "unexamined published Japanese patent application". Further, a percutaneous preparation containing estradiol which can release a definite amount of estradiol for a prolonged period of time while scarcely causing skin irritation is proposed, as described, e.g., in JP-A-2-102655.

In the aforesaid patch-type preparation containing ethanol, however, it is required to retain a large amount of a water-ethanol mixture, which makes the preparation thick. As a result, it gives a feeling of physical disorder when applied to the skin. It is sometimes observed, furthermore, that an adhesive employed for fixing the preparation onto the skin is plasticized by the ethanol and thus stains the surface of the skin.

In the case of the latter preparation described above, on the other hand, the solubility of estradiol is elevated by using an adhesive comprising a specific copolymer as the main component to thereby increase the estradiol content. Although it shows a satisfactory sustained release, therefore, it cannot be regarded as an excellent preparation from the viewpoint of the releasing dose.

Namely, because estrogen has a poor solubility in common adhesives, when a therapeutically effective amount of estrogen is added to an adhesive, the estrogen would crystallize out from the adhesive. Then, the crystals grow and thus the concentration of the dissolved estrogen is lowered, which seriously lowered the amount of the estrogen to be percutaneously absorbed. When an adhesive, in which estrogen shows a high solubility, is employed, the solubility can be elevated. In this case, however, there is a possibility that the estrogen is released only in an insufficient amount per unit time.

SUMMARY OF THE INVENTION

Under these circumstances, the present inventors have conducted extensive studies in order to solve the above problems. As a result, it has been found that a decrease in the cohesive power of the adhesive can be prevented and the stress applied to the skin surface upon the separation of the preparation can be relieved and dispersed so as to achieve well-balanced skin adhesiveness and skin irritativeness by blending an acrylate polymer, in which estrogen is highly soluble, with a relatively large amount of a liquid ingredient at a specific ratio and subjecting the thus-obtained composition to crosslinking to thereby give an oily crosslinked gel layer while preventing the crystallization of the estrogen, thus completing the present invention.

An object of the present invention is to provide an estrogen-containing percutaneous preparation capable of continuously administering estrogen to the living body.

Other objects and effects of the present invention will be apparent from the following description.

The present invention provides an estrogen-containing gel preparation which comprises a substrate having on one surface thereof a crosslinked gel layer formed by crosslinking a composition comprising the following ingredients (a) to (c), the weight ratio of the ingredient (b) to the ingredient (c) being from 1.0/0.25 to 1.0/2.0:

(a) estrogen;
(b) an acrylate polymer; and
(c) a liquid ingredient compatible with the ingredient (b).

DETAILED DESCRIPTION OF THE INVENTION

Figure 1:
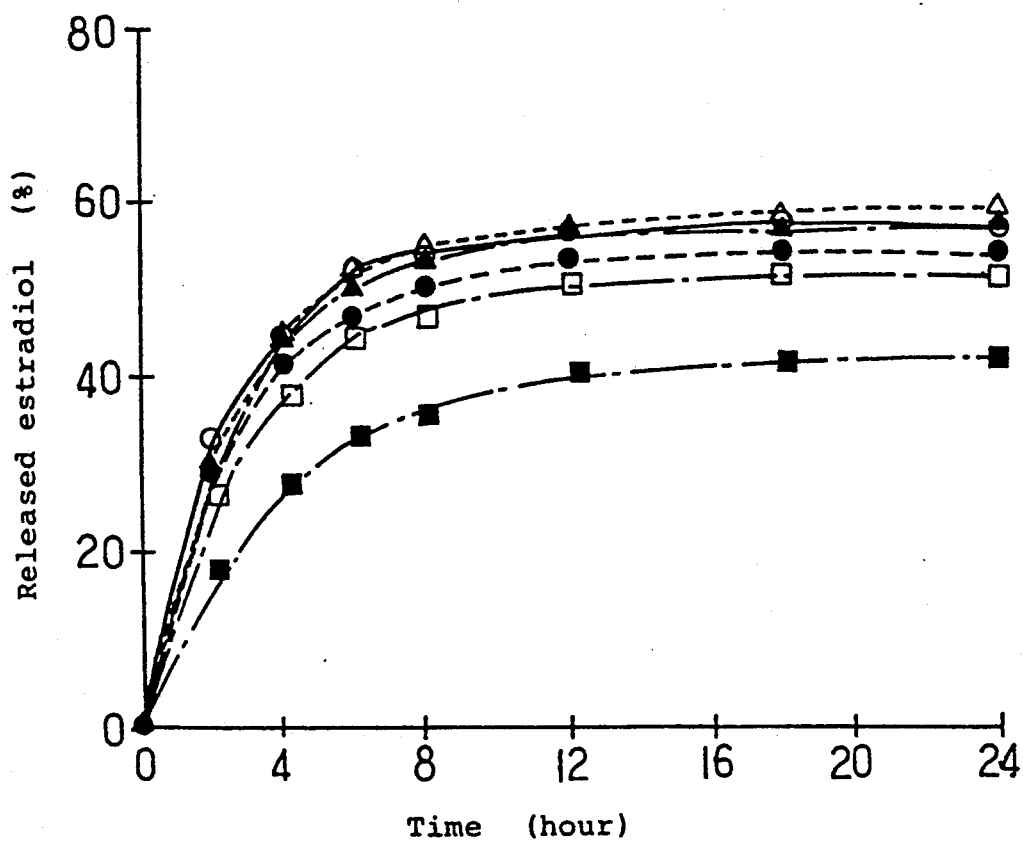
FIG. 1 is a graph which shows the results of the release in water test on gel preparations obtained in the Examples.

The substrate to be used in the estrogen-containing gel preparation of the present invention is not particularly limited, but, materials, which would never suffer from any decrease in the content of the liquid ingredient or the estrogen contained in the crosslinked gel layer caused by the migration toward another surface of the substrate followed by leakage, are preferred. Examples thereof include sole films of polyester, nylon, Saran resins, polyethylene, polypropylene, polyvinyl chloride, ethylene/ethyl acrylate copolymers, polytetrafluoroethylene, Surlyn resins and metal foils as well as laminate films comprising these materials. Among these, it is preferred to use a substrate in the form of a laminate film composed of a nonporous sheet comprising one or more materials as cited above and a porous film and to form a crosslinked gel layer on the surface of the porous sheet, so as to thereby improve the adhesiveness between the substrate and the crosslinked gel layer by the anchoring effect which will be described hereinbelow.

The material of the porous film is not particularly restricted, so long as the anchoring effect to the crosslinked gel layer can be improved. Examples thereof include paper, woven fabric, nonwoven fabric and mechanically perforated sheet. It is particularly preferred to use paper, woven fabric and nonwoven fabric therefor. When the improvement of the anchoring effect and the flexibility of the whole preparation are taken into consideration, the thickness of the porous film is preferably from 10 to 500 $\mu$m, and in the case of a thin preparation such as plaster or tape, it is more preferably from 10 to 200 $\mu$m. When the laminate film composed of the above porous film and the nonporous sheet is used as the substrate, the thickness of the nonporous sheet is preferably from 0.5 to 50 $\mu$m, and more preferably from 1 to 25 $\mu$m.

When woven fabric or nonwoven fabric is to be used as the porous film, the weight per unit area of the woven or nonwoven fabric is preferably from 5 to 30 g/m², and more preferably from 8 to 20 g/m², from the viewpoint of the improvement of the anchoring effect.

In the present invention, the crosslinked gel layer to be formed on one face of the aforesaid substrate is a layer of a crosslinked structure obtained by crosslinking a composition comprising estrogen (ingredient (a)), an acrylate polymer (ingredient (b)) and a liquid ingredient compatible with the ingredient (b) (ingredient (c)) by an arbitrary crosslinking means and having an appropriate adhesiveness to the skin and an appropriate cohesive power.

The acrylate polymer serves as a main component constituting the crosslinked gel layer together with the liquid ingredient which will be described in detail hereinafter. It sustains a high compatibility with the liquid ingredient and thus shows an excellent adhesiveness to the skin surface as well as an excellent shape retention.

In the present invention, it is not preferred to use rubber such as natural or synthetic rubber or a silicone polymer since these materials have a poor compatibility with the liquid ingredient to be used in the present invention or show a considerably low solubility or release of the pharmaceutical component. In addition, it is difficult to control the amount of functional groups participating in the crosslinking reaction of such a polymer, compared with the acrylate polymer to be used in the present invention, and thus reproducible crosslinking can hardly be achieved. Therefore, the above-mentioned polymers are unsuitable in the present invention.

As the acrylate polymer (ingredient (b)) used in the present invention, a polymer obtained by polymerizing alkyl (meth)acrylates conventionally used in the production of an adhesive as the main monomer may be employed. Among these polymers, a copolymer of an alkyl (meth)acrylate, a vinyl monomer having a saturated or unsaturated heterocyclic ring having at least one nitrogen atom on a side chain of the vinyl monomer, and (meth)acrylic acid is particularly preferably used in the present invention since it may be preferably used together with estrogen. As the alkyl (meth)acrylate, those having an alkyl group carrying 2 to 14 carbon atoms are preferred. Examples of the alkyl (meth)acrylate include (meth)acrylates having a straight-chain or branched alkyl group, for example, butyl, pentyl, hexyl, heptyl, octyl, nonyl, decyl, undecyl, dodecyl and tridecyl. Among these, 2-ethylhexyl acrylate, isooctyl acrylate and isononyl acrylate are preferably used. Either one or more of these (meth)acrylates may be used.

The terms "(meth)acrylate", etc. used herein mean "acrylate and/or methacrylate", etc.

The vinyl monomer having a saturated or unsaturated heterocyclic ring having at least one nitrogen atom on a side chain thereof copolymerized with the aforesaid (meth)acrylate is employed in order to elevate the solubility of estrogen. Examples thereof include acrylamide, vinyl pyridine, vinyl piperidine, vinyl pyrimidine, vinyl pyrazine, vinyl piperazine, vinyl pyrrolidone, methyl vinyl pyrrolidone, vinyl piperidone, vinyl pyrodin, vinyl pyrrole, vinyl imidazole, vinyl pyrazole, vinyl imidazoline, vinyl oxoazole and acryloyl morpholine. Among these, acrylamide, vinylpyrrolidone and methyl vinyl pyrrolidone are preferably used. Either one of these monomers or a mixture thereof may be used. These monomers may be replaced by their derivatives substituted with lower alkyl groups or various isomers.

In the present invention, it is preferred that the above-mentioned (meth)acrylate(s) and vinyl monomers are further copolymerized with (meth)acrylic acid. The addition of the (meth)acrylic acid, even in a small amount, would improve the cohesive power of the crosslinked gel layer. Furthermore, it exerts a useful effect in the crosslinking reaction as described in detail hereinafter.

The ratio of the above-mentioned monomers at the copolymerization may be arbitrarily selected depending on the gel properties of the target gel preparation and the release property of the estrogen. The weight ratio of the alkyl (meth)acrylate/the vinyl monomer having a saturated or unsaturated heterocyclic ring having at least one nitrogen atom as a side chain/the (meth)acrylic acid is preferably (54.2–90)/(4–39.8)/(0.2–6), more preferably (89–63)/(10–32)/(1–5), with the total amount of these comonomers being 100.

The liquid ingredient (ingredient (c)) used in the present invention has a high compatibility with the above-mentioned acrylate polymer (ingredient (b)). The ingredient (c) moderately plasticizes the crosslinked gel layer and thus imparts a flexible texture, to thereby relive a pain or skin irritativeness caused by the skin adhesiveness upon the separation of the crosslinked gel layer from the skin surface. Since the crosslinked gel layer is plasticized thereby, furthermore, the estrogen contained in the crosslinked gel layer can be freely dispersed, thus achieving an improved release property. Therefore, the liquid ingredient may be selected from among materials having a plasticizing effect. A substance which further has an absorption-promoting effect may be selected therefor to thereby improve the percutaneous absorption of the pharmaceutical component used together.

Examples of the liquid ingredient include fats and oils such as olive oil, castor oil, squalane and lanolin; organic solvents such as dimethyl decyl sulfoxide, methyl octyl sulfoxide, dimethyl sulfoxide, dimethylformamide, dimethylacetamide, dimethyllaurylamide, dodecylpyrrolidone and isosorbitol; liquid surfactants; plasticizers such as diisopropyl adipate, phthalates and diethyl sebacate; hydrocarbons such as liquid paraffin; ethoxylated stearyl alcohol, glycerol esters, isopropyl myristate, isotridecyl myristate, ethyl laurate, N-methylpyrrolidone, ethyl oleate, oleic acid, isopropyl adipate, isopropyl palmitate, octyl palmitate and 1,3-butanediol. Among the above, isopropyl myristate, isotridecyl myristate, ethyl oleate and octyl palmitate are preferably used. Either one of these substances or a mixture thereof may be used.

The aforesaid acrylate polymer (ingredient (b)) and the aforesaid liquid ingredient (ingredient (c)) are preferably contained in the crosslinked gel layer at a weight ratio of from 1.0/0.25 to 1.0/2.0, more preferably from 1.0/0.4 to 1.0/2.0 and still preferably from 1.0/0.6 to 1.0/1.8. In contrast, a conventional preparation usually contains a liquid ingredient at a weight ratio less than 1.0/0.25. Such a low content of the liquid ingredient would sometimes make it impossible to achieve a satisfactory percutaneous absorption of estrogen from a practical viewpoint.

In the present invention, the ingredients (a) to (c) are blended together and then crosslinked by an appropriate crosslinking procedure so as to give a gel, thus preventing the leakage of the liquid ingredient contained in the preparation and imparting a cohesive power, as described above. Usually, the aforesaid ingredient (b) would undergo the crosslinking reaction. The crosslinking may be effected by a physical means such as irradiation (for example, UV irradiation or electron beam irradiation) or a chemical means with the use of a crosslinking agent (for example, polyisocyanate compound, organic peroxide, organic metal salt, metal alcholate, metal chelate compound, polyfunctional compound).

Among these crosslinking procedures, irradiation or the use of an organic peroxide might sometimes induce decomposition. Further, the use of a highly reactive isocyanate or a metal salt or an organic metal salt commonly used in crosslinking reactions might sometimes cause an increase in the viscosity of the solution, which lowers the workability thereof. It is also possible to preliminarily copolymerize a polyfunctional monomer such as diacrylate with the acrylate polymer. In this case, however, there is a possibility that the viscosity of the solution would increase at the polymerization.

In the present invention, therefore, it is preferred to select a trifunctional isocyanate or a metal alcholate or a metal chelate compound comprising titanium or aluminum from among the aforesaid crosslinking agents, from the viewpoints of reactivity and handling. These crosslinking agents would not cause any increase in the viscosity of the solution until the completion of the application and drying, which means that they are excellent in workability. When these corsslinking agents are used, the crosslinking reaction can be effected to a certain extent by coating and drying the gel layer, but the coated and dried gel layer is preferably aged at from 40° to 70° C. for stabilizing the properties of the gel layer. The aging time varies depending on the addition amount and the kind of the functional groups of the crosslinking agent, and is generally from 2 to 3 days. Such a crosslinking agent is preferably used in an amount of from 0.01 to 2.0 parts by weight per 100 parts by weight of the acrylate polymer. When the acrylate polymer has no such a functional group as to react with the above-mentioned crosslinking agent, it may be modified by, for example, treating with an alkali to thereby enable the crosslinking.

The crosslinked gel layer in the present invention contains estrogen as an active ingredient. Either a steroid estrogen or a synthetic estrogen may be used as the estrogen. Examples of the steroid estrogen include estrone, estradiol, estriol, ethynyl estradiol, mestranol, estradiol benzoate and estradiol valerate. Examples of the synthetic estrogen include diethylstilbestrol and hexestrol. The content of estrogen may be appropriately determined depending on the purpose of the administration. It is generally contained in the crosslinked gel layer in an amount of 20% by weight or less, preferably from 1 to 10% by weight and more preferably from 1 to 6% by weight. When the content of estrogen exceeds 20% by weight, no effect due to the increase in amount is generally achieved any more and, furthermore, the crystallization of the estrogen may be observed, which brings about economical disadvantages.

The method for preparing the estrogen-containing gel preparation according to the present invention is not particularly limited. For example, an acetone solution of estrogen is added to a solution of an acrylate polymer followed by stirring, and a liquid ingredient is added thereto to form a uniform solution. A crosslinking agent in the form of a solution is added to the above-ontained solution and the viscosity of the resulting solution is adjusted by ethyl acetate to prepare a gel layer coating composition. The coating composition is coated on a separator, and then dried to form a gel layer. The thickness of the gel layer after drying is preferably from 10 to 300 $\mu$m, and more preferably from 40 to 150 $\mu$m. The resulting gel layer is transferred to a substrate, and then, if necessary, aged at from 40° to 70° C. to obtain an estrogen-containing gel preparation according to the present invention.

When estrogen is to be added to the crosslinked gel layer, it is preferred that the crosslinked gel layer contains the estrogen as described above. Alternately, it is possible that the estrogen is not contained in the crosslinked gel layer but dissolved in an appropriate solvent and the solution thus-obtained is located at the interface between the crosslinked gel layer and the substrate followed by sealing the periphery of the preparation. When estrogen is separated from the crosslinked gel layer in such a manner as described above, the estrogen can be stably maintained upon storage. In this case, the release of the estrogen can be severely controlled by locating a microporous film between the layer containing the estrogen and the crosslinked gel layer.

The estrogen-containing gel preparation of the present invention, which has the aforesaid structure, comprises a crosslinked gel layer containing the acrylate polymer and a relatively large amount of the liquid ingredient compatible with the acrylate polymer. Thus, it is possible to impart a flexibility to the crosslinked gel layer and to reduce the skin irritativeness while maintaining the cohesive powder of the gel layer. When the preparation of the present invention is to be separated from the surface of the skin, therefore, the pain and skin irritativeness caused by the adhesiveness can be reduced. Thus, the estrogen-containing gel preparation of the present invention has well-balanced adhesiveness to the skin and non-irritativeness. Furthermore, the estrogen-containing gel preparation of the present invention is in the form of a gel in which estrogen is highly soluble. Thus, the degree of freedom of the migration of the estrogen contained in the preparation is high, which secures excellent release of the estrogen and the subsequent percutaneous absorption of the same.

The estrogen-containing gel preparation is available for the treatment of any disease which may be treated by the administration of estrogen. Thus, the estrogen-containing gel preparation of the present invention may be useful for preventing and treating, for example, fragilitas ossium, prostatic cancer, amenorrhea, anovulatory cycle, abnormal menstrual cycle (suppressed or multiple menses), emmeniopathy (hypomenorrhea or hypermenorrhea), dysmenorrhea, menometrohhagia, uterine hypoplasia, ovarian defect, menopausal syndrome, oligogalactia and infertility of man and animal.

The dose of estrogen by the estrogen-containing gel preparation of the present invention may be widely varied depending on the man and animal to be treated, the severity of the condition and the diagnosis of a physician. When the gel preparation is applied to the skin, the estrogen is generally released at a rate of 0.1 to 3 $\mu$g/cm$^2$/hr, and preferably 0.3 to 1 $\mu$g/cm$^2$/hr.

As a matter of course, it may be administered in a dose smaller than the lower limit or exceeding the upper limit as specified above depending on the severity of the condition of the patient or diagnosis of a physician, as described above. The aforesaid preparation of the present invention may be continuously administered for from a day to several months.

The present invention will be described in more detail by referring to the following Examples and Comparative Examples, but the present invention is not construed as being limited thereto. In the following Examples and Comparative Examples, all parts and percents are by weight.

EXAMPLE 1

75 Parts of 2-ethylhexyl acrylate, 22 parts of N-vinyl-2-pyrrolidone and 3 parts of acrylic acid were copolymerized in ethyl acetate under an inert gas atmosphere to thereby give an acrylic copolymer solution.

To 47.5 parts of the solid content of the above solution, 2.5 parts of estradiol and 50 parts of isopropyl myristate was added. To 99.8 parts of the above acrylic copolymer, 0.2 parts of aluminum tris(acetylacetonate) which was in the form of a 10% solution in acetylacetone was added. Further, ethyl acetate was added thereto so as to adjust the viscosity of the mixture.

The viscous solution thus-obtained was applied to a polyester separator (thickness: 75 μm) in such a manner as to give a thickness of 40 μm after drying. After drying and crosslinking, a crosslinked gel layer was formed.

The crosslinked gel layer thus-obtained was adhered to the nonwoven fabric face of a laminate film (i.e., a substrate), which was obtained by extruding polyester having a thickness of 2 μm on a polyester nonwoven fabric (12 g/m²). Thus, a gel preparation of the present invention was obtained.

EXAMPLE 2

The procedure of Example 1 was repeated except that the isopropyl myristate was replaced by ethyl oleate and that the aluminum tris(acetylacetonate) employed as a crosslinking agent was replaced with ethyl acetate aluminum diisopropylate. Thus, a gel preparation of the present invention was obtained.

EXAMPLE 3

The procedure of Example 1 was repeated except that the isopropyl myristate was replaced by octyl palmitate and that the aluminum tris(acetylacetonate) employed as a crosslinking agent was replaced with trifunctional isocyanate ("Coronate HL" manufactured by Nippon Polyurethane Co., Ltd.). Thus, a gel preparation of the present invention was obtained.

EXAMPLE 4

The procedure of Example 1 was repeated except that the isopropyl myristate was replaced with isotridecyl myristate. Thus, a gel preparation of the present invention was obtained.

EXAMPLE 5

The procedure of Example 1 was repeated except that the estradiol was replaced with estrone. Thus, a gel preparation of the present invention was obtained.

EXAMPLE 6

The procedure of Example 1 was repeated except that the estradiol was replaced with estriol. Thus, a gel preparation of the present invention was obtained.

COMPARATIVE EXAMPLE 1

The procedure of Example 1 was repeated except that 2.5 parts of estradiol was added to 97.5 parts of the solid content of the acrylic copolymer solution obtained in Example 1 and that ethyl acetate was further added thereto so as to control the viscosity. Thus, a crosslinked percutaneous preparation free from any liquid ingredient was obtained.

COMPARATIVE EXAMPLE 2

The procedure of Comparative Example 1 was repeated except that 5 parts of estradiol was added to 95 parts of the solid content of the copolymer solution. Thus, a crosslinked percutaneous preparation free from any liquid ingredient was obtained.

COMPARATIVE EXAMPLE 3

The procedure of Comparative Example 1 was repeated except that no crosslinking agent was added. Thus, an uncrosslinked percutaneous preparation free from any liquid ingredient was obtained.

COMPARATIVE EXAMPLE 4

The procedure of Example 1 was repeated except that no crosslinking agent was added. Thus, an uncrosslinked gel preparation containing the liquid ingredient was obtained.

This gel preparation was broken because of low cohesive power. Thus, it could not be subjected to the test which will be described hereinafter.

COMPARATIVE EXAMPLE 5

The procedure of Example 1 was repeated except that 2.5 parts of estradiol and 15 parts of isopropyl myristate were added to 82.5 parts of the solid content of the acrylate copolymer solution. Thus, a crosslinked gel preparation containing the liquid ingredient was obtained.

TEST EXAMPLE

Each of the estradiol gel preparations obtained in the above Examples and Comparative Examples was cut into a piece of 20 cm² (40 mm × 50 mm) and then stored at 40° C. under a relative humidity of 75% for 2 weeks. Next, these samples were subjected to the following tests.

Figure 2:
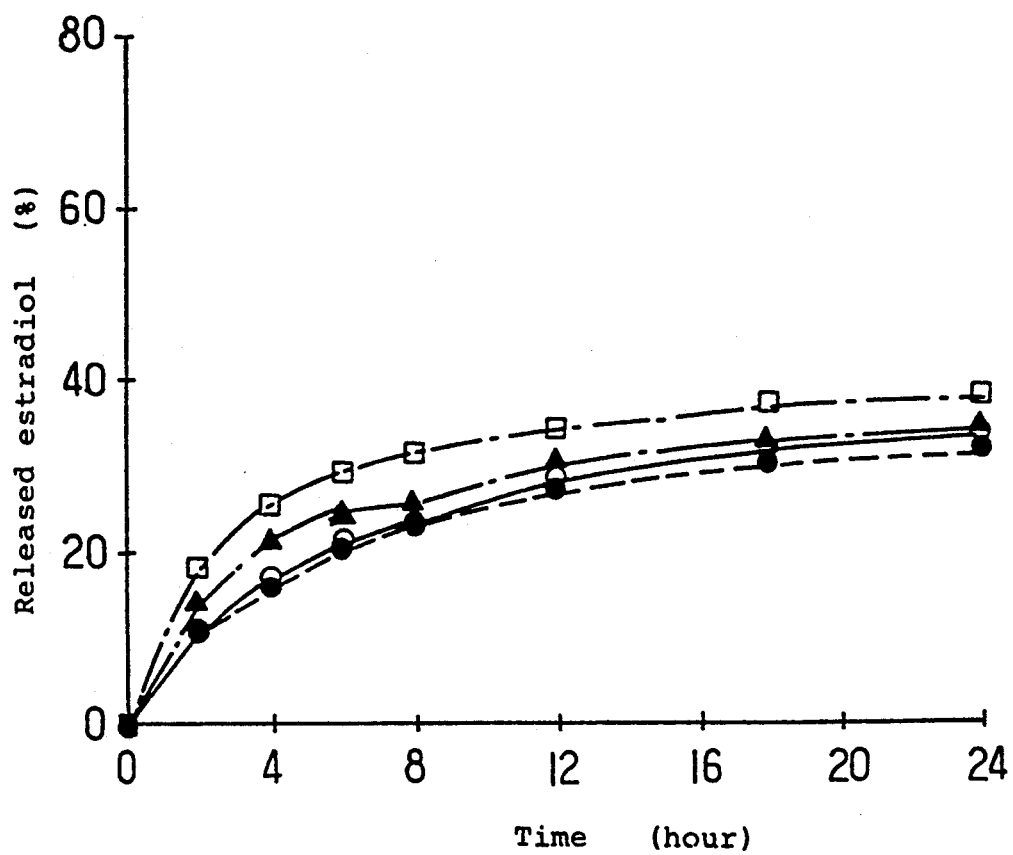
FIG. 2 is a graph which shows the results of the release in water test on preparations obtained in the Comparative Examples.

Table 1 and FIGS. 1 and 2 show the results.

Rabbit patch test

Each of the samples obtained in Examples and Comparative Examples was applied onto the dorsal part of a rabbit, from which the hair had been removed, for 48 hours. Then the amount of the estradiol migrated into the skin was determined from the difference in the estradiol contents in the sample before and after the application. The results obtained are shown in Table 1.

Release in water test

This test was performed in accordance with the paddle test specified in The Pharmacopeia of Japan.

Namely, each sample was fixed on a stainless spring and immersed in 800 ml of degassed distilled water at 32° C. Then, the water was stirred at 50 rpm and the extract was collected at definite intervals of time. Each extract sample thus obtained was subjected to high performance liquid chromatography to thereby determine the concentration of the released estradiol. The results are shown in FIGS. 1 and 2.

TABLE 1

|  | Estradiol migrated into skin (μg) |
|---|---|
| Example 1 | 1,020 ± 130 |
| Example 2 | 1,250 ± 270 |
| Example 3 | 1,220 ± 250 |
| Example 4 | 1,350 ± 100 |

TABLE 1-continued

|  | Estradiol migrated into skin (μg) |
|---|---|
| Example 5 | 990 ± 190 |
| Example 6 | 480 ± 110 |
| Comparative Example 1 | 80 ± 20 |
| Comparative Example 2 | 145 ± 35 |
| Comparative Example 3 | 100 ± 30 |
| Comparative Example 5 | 448 ± 50 |

As Table 1 and FIGS. 1 and 2 show, the estrogen-containing gel preparation according to the present invention shows the migration of an extremely large amount of estradiol into the skin and releases an extremely large amount of estradiol, compared with the comparative products.

While the invention has been described in detail and with reference to specific examples thereof, it will be apparent to one skilled in the art that various changes and modifications can be made therein without departing from the spirit and scope thereof.

What is claimed is:

1. An estrogen-containing gel preparation comprising a substrate having on one surface thereof a crosslinked gel layer formed by crosslinking a composition consisting essentially of the following ingredients (a) to (c), the weight ratio of said ingredient (b) to said ingredient (c) being from 1.0/0.25 to 1.0/2.0:
   (a) estrogen;
   (b) an acrylate polymer obtained by copolymerizing 54.2-90 parts by weight of an alkyl (meth)acrylate, 4-39.8 parts by weight of a vinyl monomer with a saturated or unsaturated heterocyclic ring having at least one nitrogen atom on a side chain of said vinyl monomer, and 0.2-6 parts by weight of (meth)acrylic acid, based on 100 parts by weight of said acrylate polymer; and
   (c) a liquid ingredient compatible with said ingredient (b), said liquid ingredient moderately plasticizing said crosslinked gel layer and imparting flexibility thereto to reduce skin irritation upon removal of said crosslinked gel layer from a skin surface;
   wherein said composition further comprises a crosslinking agent selected from a trifunctional isocyanate, a metal alcoholate, and a metal chelate compound comprising titanium or aluminum in an amount of from 0.01 to 2.0 parts by weight per 100 parts by weight of said acrylate polymer.

2. An estrogen-containing gel preparation as claimed in claim 1, wherein said ingredient (a) is estradiol.

3. An estrogen-containing gel preparation as claimed in claim 1, wherein the weight ratio of said ingredient (b) to said ingredient (c) being from 1.0/0.4 to 1.0/2.0.

4. An estrogen-containing gel preparation as claimed in claim 3, wherein the weight ratio of said ingredient (b) to said ingredient (c) being from 1.0/0.6 to 1.0/1.8.

5. An estrogen-containing gel preparation as claimed in claim 1, wherein the content of said estrogen is 20% by weight or less based on the total amount of said crosslinked gel layer.

6. An estrogen-containing gel preparation as claimed in claim 5, wherein the content of said estrogen is from 1 to 10% by weight based on the total amount of said crosslinked/gel layer.

7. An estrogen-containing gel preparation as claimed in claim 6, wherein the content of said estrogen is from 1 to 8% by weight based on the total amount of said crosslinked gel layer.

8. An estrogen-containing gel preparation as claimed in claim 1, wherein the thickness of said crosslinked gel layer is from 10 to 300 μm.

9. An estrogen-containing gel preparation as claimed in claim 1, wherein the thickness of said crosslinked gel layer is from 40 to 150 μm.

10. An estrogen-containing gel preparation as claimed in claim 1 wherein said liquid ingredient is one or a mixture of compounds selected from the group consisting of isopropyl myristate, isotridecyl myristate, ethyl oleate and octyl palmitate.

11. An estrogen-containing gel preparation as claimed in claim 1 wherein said plasticizing liquid ingredient is one or a mixture of compounds selected from the group consisting of liquid paraffin hydrocarbons, ethoxylated stearyl alcohol, glycerol esters, isopropyl myristate, isotridecyl myristate, ethyl laurate, N-methylpyrrolidone, ethyl oleate, oleic acid, isopropyl adipate, isopropyl palmitate, octyl palmitate, and 1,3-butanediol.

* * * * *